United States Patent
Robson et al.

(10) Patent No.: US 10,653,641 B2
(45) Date of Patent: May 19, 2020

(54) USE OF CANNABINOIDS IN THE TREATMENT OF MENTAL DISORDERS

(71) Applicant: GW Pharma Limited, Histon, Cambridge, Cambridgeshire (GB)

(72) Inventors: Philip Robson, Histon (GB); Geoffrey Guy, Histon (GB); Stephen Wright, Histon (GB); Emma Cheetham, Histon (GB); Dominic Schiller, Birkenhead (GB)

(73) Assignee: GW Pharma Limited, Cambridge (GB)

( * ) Notice: Subject to any disclaimer, the term of this patent is extended or adjusted under 35 U.S.C. 154(b) by 0 days.

(21) Appl. No.: 15/757,899

(22) PCT Filed: Sep. 8, 2016

(86) PCT No.: PCT/GB2016/052778
§ 371 (c)(1),
(2) Date: Mar. 6, 2018

(87) PCT Pub. No.: WO2017/042567
PCT Pub. Date: Mar. 16, 2017

(65) Prior Publication Data
US 2018/0344660 A1    Dec. 6, 2018

(30) Foreign Application Priority Data

Sep. 9, 2015 (GB) .................................. 1515986.6

(51) Int. Cl.
| | |
|---|---|
| A61K 31/05 | (2006.01) |
| A61P 25/18 | (2006.01) |
| A61K 31/496 | (2006.01) |
| A61K 31/551 | (2006.01) |
| A61K 31/5513 | (2006.01) |
| A61K 31/40 | (2006.01) |
| A61K 31/519 | (2006.01) |
| A61K 31/554 | (2006.01) |

(52) U.S. Cl.
CPC ............ *A61K 31/05* (2013.01); *A61K 31/40* (2013.01); *A61K 31/496* (2013.01); *A61K 31/519* (2013.01); *A61K 31/551* (2013.01); *A61K 31/554* (2013.01); *A61K 31/5513* (2013.01); *A61P 25/18* (2018.01)

(58) Field of Classification Search
None
See application file for complete search history.

(56) References Cited

U.S. PATENT DOCUMENTS

2011/0038958 A1 * 2/2011 Kikuchi

FOREIGN PATENT DOCUMENTS

| WO | WO 2003/087037 A1 | 10/2003 |
|---|---|---|
| WO | WO 2006/017892 A1 | 2/2006 |
| WO | WO 2007/136571 A1 | 11/2007 |
| WO | WO 2009/087351 A1 | 7/2009 |
| WO | WO 2015/065179 A1 | 5/2015 |
| WO | WO 2017/042567 A1 | 3/2017 |

OTHER PUBLICATIONS

Deiana, Medical use of cannabis. Cannabidiol: a new light for schizophrenia? Drug Test Anal. Jan. 2013;5(1):46-51. doi: 10.1002/dta.1425. Epub Oct. 25, 2012.
Gomes et al., Decreased glial reactivity could be involved in the antipsychotic-like effect of cannabidiol. Schizophr Res. May 2015;164(1-3):155-63. doi:10.1016/j.schres.2015.01.015. Epub Feb. 10, 2015.
Gururajan, Cannabidiol and clozapine reverse MK-801 induced deficits in social interaction and hyperactivity in Sprague-Dawley rats. J. Psychopharmacology. 2012;26(10):1317-32.
Iseger et al., A systematic review of the antipsychotic properties of cannabidiol in humans. Schizophr Res. Mar. 2015;162(1-3):153-61. doi:10.1016/j.schres.2015.01.033. Epub Feb. 7, 2015.
Leweke et al., Cannabidiol enhances anandamide signaling and alleviates psychotic symptoms of schizophrenia. Transl Psychiatry. Mar. 20, 2012;2:e94. doi:10.1038/tp.2012.15.
Robson et al., Cannabinoid and Schizophrenia: Therapeutic Prospects. Current Pharmaceutical Design, 2014;20(13):2194-204.
Shoval et al., Prohedonic Effect of Cannabidiol in a Rat Model of Depression. Neuropsychobiology. 2016;73(2):123-9. doi: 10.1159/000443890. Epub Mar. 25, 2016.

(Continued)

*Primary Examiner* — Jeffrey S Lundgren
*Assistant Examiner* — Gregg Polansky
(74) *Attorney, Agent, or Firm* — Wolf, Greenfield & Sacks, P.C.

(57) ABSTRACT

This invention relates to the use of CBD to treat mental disorders. For example it can be used as an adjunct therapy to treat positive symptoms in mental disorders such as schizophrenia and related disorders; or as an adjunct therapy in combination with olanzapine to treat both positive and negative symptoms in mental disorders such as schizophrenia and related disorders; or as an adjunct therapy in combination with olanzapine to treat negative symptoms in mental disorders such as schizophrenia and related disorders; or as an adjunct therapy to treat anhedonia/asociality in mental disorders such as schizophrenia and related disorders; or as an adjunct therapy to treat avolition/apathy in mental disorders such as schizophrenia and related disorders; or as an adjunct therapy to treat disturbance of attention in mental disorders such as schizophrenia and related disorders; or as a monotherapy or as an adjunct therapy to treat one or more distinct sub-domains of negative symptoms selected from: i) avolition/apathy; ii) anhedonia/asociality and iii) disturbance of attention; or as an adjunct therapy to treat cognitive symptoms, particularly working memory, motor speed and executive function in mental disorders such as schizophrenia and related disorders. There may additionally be provided compositions comprising CBD in combination with one or more antipsychotics such as olanzapine and quetiapine. In particular the invention relates to the treatment of schizophrenia or related psychotic disorders, more particularly still those which are considered to be treatment resistant.

7 Claims, No Drawings

(56) References Cited

OTHER PUBLICATIONS

Taylor et al., Cannabidiol reverses MK-801 induced social withdrawal in rats. Acta Pharmacologica Sinica, 2006;27(1):78, Meeting Abstract.
Zuardi, Cannabidiol: from an inactive cannabinoid to a drug with wide spectrum of action. Braz J Psychiatry. Sep. 2008;30(3):271-80.
Zuardi et al., Cannabidiol was ineffective for manic episode of bipolar affective disorder. J Psychopharmacol. Jan. 2010;24(1):135-7. doi: 10.1177/0269881108096521. Epub Sep. 18, 2008.

* cited by examiner

USE OF CANNABINOIDS IN THE TREATMENT OF MENTAL DISORDERS

RELATED APPLICATION

This application is a national stage filing under 35 U.S.C. § 371 of International Application No. PCT/GB2016/052778, filed Sep. 8, 2016, which was published under PCT Article 21(2) in English, the entire disclosure of which is incorporated by reference herein in its entirety.

FIELD OF THE INVENTION

This invention relates to the use of cannabinoids in the treatment of mental disorders.

In the United States, the Diagnostic and Statistical Manual of Mental Health (DSM) serves as the universal authority for psychiatric diagnosis. DSM-V, published in 2013, supersedes DSM-IV, published 2000, which defined the symptoms of schizophrenia as including: (1) delusions, (2) hallucinations, (3) disorganized speech (e.g. frequent derailment or incoherence), (4) grossly disorganized or catatonic behaviour; and (5) negative symptoms i.e. affective flattening, alogia (poverty of speech), or avolition (lack of motivation).

The symptoms of schizophrenia fall into three broad categories: (1) positive symptoms, (2) negative symptoms, and (3) cognitive symptoms.

Broadly speaking, positive symptoms include hallucinations, delusions, thought disorders and movement disorders; negative symptoms include "flat affect", lack of pleasure in everyday life, lack of ability to begin and sustain planned activities, and speaking little, even when forced to interact; and cognitive symptoms include poor "executing function"; trouble focussing or paying attention, and problems with "working memory", (National Institute of Mental Health). Treatment is generally with antipsychotic medications (typical and atypical antipsychotics).

More particularly the invention relates to:
1. The use of CBD as an adjunct therapy to treat positive symptoms in mental disorders such as schizophrenia and related disorders;
2. The use of CBD as an adjunct therapy in combination with olanzapine to treat both positive and negative symptoms in mental disorders such as schizophrenia and related disorders;
3. The use of CBD as an adjunct therapy in combination with olanzapine to treat negative symptoms in mental disorders such as schizophrenia and related disorders;
4. The use of CBD as an adjunct therapy to treat anhedonia/asociality in mental disorders such as schizophrenia and related disorders;
5. The use of CBD as an adjunct therapy to treat avolition/apathy in mental disorders such as schizophrenia and related disorders;
6. The use of CBD as an adjunct therapy to treat disturbance of attention in mental disorders such as schizophrenia and related disorders;
7. The use of CBD as a monotherapy or as an adjunct therapy to treat one or more distinct sub-domains of negative symptoms selected from: i) avolition/apathy; ii) anhedonia/asociality and iii) disturbance of attention.
8. The use of CBD as an adjunct therapy to treat cognitive symptoms, particularly working memory, motor speed and executive function in mental disorders such as schizophrenia and related disorders; and
9. Compositions comprising CBD in combination with one or more antipsychotics such as olanzapine and quetiapine.

In particular the invention relates to the treatment of schizophrenia or related psychotic disorders, more particularly still those which are considered to be treatment resistant.

BACKGROUND TO THE INVENTION

Schizophrenia is a psychiatric diagnosis that describes a mental illness characterised by impairments in the perception or expression of reality, most commonly manifesting as auditory hallucinations, paranoid or bizarre delusions or disorganised speech and thinking in the context of significant social or occupational dysfunction.

Onset of symptoms typically occurs in young adulthood (Castle et al. 1965), with approximately 0.4-0.6% of the population affected (Goldner et al. 2002). Diagnosis is based on the participant's self-reported experiences and observed behaviour. Schizophrenia occurs equally in males and females although it typically appears earlier in men with the peak ages of onset being 20-28 years for males and 26-32 years for females. Much rarer are instances of childhood-onset and late- (middle age) or very-late-onset (old age) schizophrenia.

The lifetime prevalence of schizophrenia, that is, the proportion of individuals expected to experience the disease at any time in their lives, is commonly given at 1%.

Schizophrenia is known to be a major cause of disability. In a 1999 study of 14 countries, active psychosis was ranked the third-most-disabling condition after quadriplegia and dementia, and before paraplegia and blindness (Robson et al. 2014).

Studies suggest that genetics, early environment, neurobiology and psychological and social processes are important contributory factors. Current psychiatric research is focused on the role of neurobiology, but no single organic cause has been found. Due to the many possible combinations of symptoms, there is debate about whether the diagnosis represents a single disorder or a number of discrete syndromes.

Schizophrenia is often described in terms of positive (or productive) and negative (or deficit) symptoms (Sims, 2002). Positive symptoms include delusions, auditory hallucinations, and thought disorder, and are typically regarded as manifestations of psychosis. Negative symptoms are so-named because they are considered to be the loss or absence of normal traits or abilities, and include features such as flat or blunted affect and emotion, poverty of speech (alogia), anhedonia, and lack of motivation (avolition).

Despite the appearance of blunted affect, recent studies indicate that there is often a normal or even heightened level of emotionality in schizophrenia, especially in response to stressful or negative events (Cohen and Docherty, 2004).

A third symptom grouping, the disorganisation syndrome, is commonly described, and includes chaotic speech, thought, and behaviour. There is also evidence for a number of other symptom classifications. The disorder is also thought to affect cognition, which also usually contributes to chronic problems with behaviour and emotion.

People diagnosed with schizophrenia are likely to be diagnosed with comorbid conditions, including clinical depression and anxiety disorders; the lifetime prevalence of substance abuse is typically around 40%. Social problems, such as long-term unemployment, poverty and homelessness, are common and life expectancy is decreased; the average life expectancy of people with the disorder is 10 to 12 years less than those without, owing to increased physical health problems and a high suicide rate.

Social isolation commonly occurs and may be due to a number of factors. Impairment in social cognition is associated with schizophrenia, as are the active symptoms of paranoia from delusions and hallucinations, and the negative symptoms of apathy and avolition. Many people diagnosed with schizophrenia avoid potentially stressful social situations that may exacerbate mental distress (Freeman et al. 2007).

Late adolescence and early adulthood are peak years for the onset of schizophrenia. These are critical periods in a young adult's social and vocational development, and they can be severely disrupted by disease onset.

Schizophrenia has three phases: prodromal, active and residual. These phases tend to happen in order and appear in cycles throughout the course of the illness. During a lifetime, people with schizophrenia may become actively ill once or twice, or have many more episodes.

In the prodromal phase, people start to lose interest in their usual activities and to withdraw from friends and family members. They may become easily confused, have trouble concentrating, and feel listless and apathetic, preferring to spend most of their days alone. They may also become intensely preoccupied with religion or philosophy. This phase can last weeks or months.

During schizophrenia's active phase, people may have delusions, hallucinations, marked distortions in thinking and disturbances in behaviour and feelings. This phase is often the most frightening to the person with schizophrenia, and to others.

After an active phase, people may be listless, have trouble concentrating and be withdrawn. The symptoms in this residual phase are similar to those that occur during the prodromal phase.

To minimise the effect of schizophrenia, much work has recently been done to identify and treat the prodromal (pre-onset) phase of the illness, which has been detected up to 30 months before the onset of symptoms, but may be present longer (Addington et al. 2007). Those who go on to develop schizophrenia may experience the non-specific symptoms of social withdrawal, irritability and dysphoria in the prodromal period, and transient or self-limiting psychotic symptoms in the prodromal phase before psychosis becomes apparent (Robson et al. 2014).

Increased dopaminergic activity in the mesolimbic pathway of the brain is a consistent finding in schizophrenia. The mainstay of treatment to date has been focussed on pharmacotherapy with antipsychotic medications; these primarily work by suppressing/regulating dopamine activity.

A fundamental barrier to the discovery and development of novel treatments for schizophrenia has been the level of understanding of the biological processes involved in schizophrenia which, to date, has not been sufficient to predict the therapeutic value of novel drug targets. This lack of understanding has limited the ability to develop effective treatments to address the negative symptoms and cognitive impairment of schizophrenia.

The introduction into clinical practice of chlorpromazine in the mid-1950s revolutionised the treatment of the psychotic manifestations of schizophrenia and triggered the development of dozens of alternative antipsychotic medications.

A decade or so later, the synthesis of clozapine and the unanticipated discovery of its antipsychotic effects led in time to a new 'second generation' cohort of drugs that lacked the characteristic unwanted extrapyramidal effects of the 'typical' antipsychotic medications.

The pharmacological profiles of the many 'atypical' drugs currently available vary widely, but it remains the case that all of them rely primarily for their efficacy upon their effects at the dopamine D2 receptor (Miyamoto et al. 2005).

Approximately one third of first episode psychosis participants fail to respond adequately to a standard typical or atypical antipsychotic medication, and non-responders have been found to incur health costs that are twice those of responders. Recent analyses suggest little if any difference in overall efficacy between the typicals and atypicals.

Clozapine stands alone in its ability to produce a therapeutic response in participants resistant to all other antipsychotics although the pharmacological mechanism by which it achieves this response remains unknown. Unfortunately its clinical utility is limited by its propensity to cause agranulocytosis and the consequent need for haematological monitoring, along with epileptic seizures and other serious unwanted effects (Lindstrom, 1998).

The endocannabinoid system (ECS), first discovered in the early 1990s, consists of cannabinoid receptors, endogenous ligands ('endocannabinoids'), and proteins for endocannabinoid synthesis and degradation. Two G protein-coupled receptors for cannabinoids have so far been identified, designated cannabinoid receptor-1 ($CB_1$) and cannabinoid receptor-2 ($CB_2$).

$CB_1$ receptors are located predominantly at the presynaptic terminals of central and peripheral neurons, their main role being to mediate inhibition of neurotransmitter release. However, they are also expressed in several peripheral structures not exclusively within nervous tissue including those controlling metabolism, hormone release (e.g. cortisol and adrenaline levels), and the immune response.

$CB_2$ receptors are expressed mainly by immune cells, through which they modulate the release of both pro- and anti-inflammatory cytokines. Accumulating evidence suggests they may also be found in neurones.

This wide distribution of the receptors accounts for the breadth of influence of the ECS on immune response, learning, food intake, energy homeostasis, pain transduction, emotion, perception, behavioural reinforcement, motor co-ordination, regulation of body temperature and wake/sleep cycle, hormonal function, bone formation and apoptosis.

The activity of the ECS within the CNS is essential for normal mental health. $CB_1$ receptors are densely expressed in the cortex, hippocampus, amygdala, basal ganglia, and cerebellum. Of relevance to schizophrenia, $CB_1$ modulates release of dopamine and glutamate (as well as gamma-aminobutyric acid, serotonin, glycine, acetylcholine, and noradrenaline), and in participants their expression is increased in prefrontal cortex and anterior cingulate cortex. $CB_1$ knockout mice show increased emotional reactivity, hypersensitivity to stress, reduced responsiveness to rewarding stimuli, increased aggression to intruders, enhanced development of learned helplessness, impaired extinction of aversive memories, and social withdrawal (Robson et al, 2014).

Raised levels of anandamide have been found in the cerebrospinal fluid of untreated schizophrenia participants in comparison with controls and participants with dementia or depression. Raised blood levels of anandamide have also been found in untreated schizophrenia participants, and these were reduced after clinical remission following olanzapine treatment (De Marchi et al. 2003). Although a strong case can be made for heightened ECS activity, the $CB_1$ antagonist rimonabant had no effect on positive or negative symptoms of schizophrenia in a placebo-controlled clinical trial.

The cannabinoid cannabidiol, (CBD), appears to exhibit antipsychotic properties, and thus may be used in the treatment of schizophrenia, or more precisely the positive symptoms, namely hallucinations, delusions and confused thoughts (thought disorder).

An extensive review of the antipsychotic properties of CBD by Iseger et al. in 2015, which reviewed and referenced 29 studies incorporated by reference, concluded that CBD was an effective, safe and well tolerated antipsychotic compound, and thus may be a promising new agent in the treatment of schizophrenia.

It has been postulated that CBD may have potential utility in schizophrenia, not only as an antipsychotic but also in the alleviation of the metabolic and inflammatory abnormalities associated with the disease.

The negative symptoms of schizophrenia are discussed in detail in Foussias and Remington, 2010. The article explains that in the 1950's the introduction of chloropromazine revolutionised the treatment of major mental disorders, including schizophrenia, alleviating the positive symptoms (delusions/hallucinations) but it was not until the mid-70's early 80's that attention turned to the role of the deficit or negative symptoms.

Negative symptoms have been categorised into specific sub domains and many studies have focussed on the Scale for the Assessment of Negative Symptoms (SANS). SANS is a rating scale used to measure the negative symptoms in schizophrenia. The SANS scale consists of 5 subscales: (i) Affective flattening or blunting; (ii) Alogia; (iii) Avolition/apathy; (iv) Anhedonia/asociality; and (v) Attentional impairment.

It would be desirable to have drugs that could target these domains.

As well as negative symptoms, cognitive symptoms have been implicated as playing a substantial role in schizophrenia and both are evident at the time first episode psychosis occurs, and neither are improved substantially with existing antipsychotic treatments.

Thus, it would be desirable to have drugs that additionally targeted cognitive symptoms.

That negative and cognitive symptoms are separate domains is becoming apparent and the cognitive symptoms are generally regarded as comprising social cognition and neuro cognition and some of these aspects have traditionally been considered as/alongside negative symptoms (see for example Sergi et al. 2007).

The FDA has indicated that currently available drug treatments for schizophrenia have not been found to be satisfactory for the treatment of negative symptoms (Laughren and Levin, 2006).

It is noted that whilst almost all antipsychotic medications are targeted to the disease entity e.g. schizophrenia, as opposed to specific aspects of the disease, the FDA has now recognised that for complex psychiatric diseases there is a need to treat distinct aspects of the disease. Indeed the FDA has recently approved medications to be used in, for example, the treatment of "agitation" or "suicidality" in schizophrenia.

Furthermore they have endorsed the view that, for example "cognitive impairment" is a legitimate target in schizophrenia and that claims to a non-specific symptom not limited to a single disease entity would be appropriate.

A starting point for considering the claimed invention is WO 2009/087351, which discloses the use of cannabinoids in combination with an antipsychotic medicament. Generally it teaches that a number of phytocannabinoids (8 are specifically disclosed) may be used in combination with a number of antipsychotic medicaments (12 are specifically disclosed) to treat psychosis or a psychotic disorder (13 are specifically disclosed). The teaching is based on three lists (phytocannabinoid, antipsychotic medication and disease subsets) offering a total of 1,248 possible combinations. Of these combinations the detailed description exemplifies two specific combinations: CBD and aripiprazole; or THCV and aripiprazole, where the addition of the cannabinoid is for the purpose of improving the side effect profile of the aripiprazole by reducing catalepsy and ptosis.

A difference between WO 2009/087351 and the present invention is that it has been demonstrated, in human subjects, that providing cannabidiol (CBD) in combination with either olanzapine, aripiprazole or quetiapine (in contrast to 8 other antipsychotics) provided unexpected, and statistically significant outcomes, that could significantly improve treatments for a group of patients including those that may be considered to be treatment resistant.

Very significantly, the different technical effects achieved, enable new treatments to be offered. These new treatments include (but are not limited to): Targeting new patient groups (e.g. treatment resistant patients); Targeting a different phase of illness (e.g. prodromal, active or residual phase); Improving symptomatic relief (e.g. positive symptoms); Targeting different symptoms (e.g. negative symptoms (as opposed to positive symptoms); or Targeting specific domain subsets (e.g. Avolition/apathy, Anhedonia/asociality and disturbance of attention); or Providing a treatment or a combination medication that hits multiple targets (e.g. targets positive and/or negative symptoms and/or social cognition and/or neuro cognition).

A paper by Zuardi et al. (2010) describes the use of CBD in the treatment of two female patients with bipolar affective disorder. One patient was taking olanzapine as an adjunct therapy during the 30 days she was provided with CBD the other took CBD as a monotherapy. Zuardi states that CBD was ineffective in both patients with this disorder.

Taylor (2006) and Gururajan et al. (2012) describe the ability of CBD to reverse social deficits in rats treated with MK-801.

Deiana (2013) and Gomes et al. (2015) provide a review of the potential medical use of cannabidiol in the treatment of schizophrenia.

BRIEF SUMMARY OF THE DISCLOSURE

In accordance with a first aspect of the present invention there is provided cannabidiol (CBD) as an adjunct medicament in the treatment of a mental disorder where psychotic symptoms are being treated with a typical or an atypical antipsychotic, characterised in that the CBD is for use in augmenting the effect of the antipsychotic medicament.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is aripiprazole or a metabolite thereof.

Preferably the mental disorder is schizophrenia or a related psychotic disorder. In one embodiment the mental disorder is a treatment resistant schizophrenia.

In a further embodiment of the invention the treatment is targeted at an active phase of the schizophrenia or related disorder.

In accordance with a second aspect of the present invention there is provided a method of treating a mental disorder, in which the subject is taking a typical or an atypical antipsychotic to treat symptoms of psychosis, further comprising administering cannabidiol (CBD) to said subject in an amount, and for the purpose of, augmenting the effect of the antipsychotic.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is aripiprazole or a metabolite thereof.

Preferably the mental disorder is schizophrenia or a related psychotic disorder. More preferably the subject is deemed treatment resistant.

In a further embodiment of the invention the treatment is targeted at an active phase of the schizophrenia or related disorder.

Preferably the subject is a human.

In accordance with a third aspect of the present invention there is provided cannabidiol (CBD) as an adjunct medicament in the treatment of a mental disorder where psychotic symptoms are being treated with olanzapine, characterised in that the CBD is for use in augmenting the effect of the olanzapine and additionally treating negative symptoms and/or general symptoms of the mental disorder.

Preferably the mental disorder is schizophrenia or a related psychotic disorder. In one embodiment the mental disorder is a treatment resistant schizophrenia.

In a further embodiment of the invention the treatment is targeted at an prodromal, active or residual phase of the schizophrenia or related disorder.

In accordance with a fourth aspect of the present invention there is provided a method of treating a mental disorder, in which the subject is taking olanzapine to treat symptoms of psychosis further comprising administering cannabidiol (CBD) to said subject in an amount, and for the purpose of, augmenting the antipsychotic effects and additionally treating negative symptoms and/or general symptoms.

Preferably the mental disorder is schizophrenia or a related psychotic disorder. More preferably the subject is deemed treatment resistant.

In a further embodiment of the invention the treatment is targeted at a prodromal, active or residual phase of the schizophrenia or related disorder.

Preferably the subject is a human.

In accordance with a fifth aspect of the present invention there is provided cannabidiol (CBD) as an adjunct medicament in the treatment of a mental disorder where psychotic symptoms are being treated with olanzapine, characterised in that the CBD is for treating negative symptoms of the mental disorder.

Preferably the negative symptom to be treated is avolition/apathy. More preferably the avolition/apathy is characterised by impersistence at work or school.

Alternatively the negative symptom to be treated is anhedonia or asociality.

Preferably the mental disorder is schizophrenia or a related psychotic disorder. In one embodiment the mental disorder is a treatment resistant schizophrenia.

In a further embodiment of the invention the treatment is targeted at a prodromal or residual phase of the schizophrenia or related disorder.

In accordance with a sixth aspect of the present invention there is provided a method of treating a mental disorder, in which the subject is taking olanzapine to treat symptoms of psychosis, further comprising administering cannabidiol (CBD) to said subject in an amount, and for the purpose of, treating negative symptoms of said mental disorder.

Preferably the negative symptom to be treated is avolition/apathy. More preferably the avolition/apathy is characterised by impersistence at work or school.

Alternatively the negative symptom to be treated is anhedonia or asociality.

Preferably the mental disorder is schizophrenia or a related psychotic disorder. More preferably the subject is deemed treatment resistant.

In a further embodiment of the invention the treatment is targeted at a prodromal or residual phase of the schizophrenia or related disorder.

Preferably the subject is a human.

In accordance with a seventh aspect of the present invention there is provided cannabidiol (CBD) as an adjunct medicament in the treatment of a mental disorder where psychotic symptoms are being treated with a typical or an atypical antipsychotic, characterised in that the CBD is for use in treating anhedonia or asociality.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine or quetiapine.

Preferably the mental disorder is schizophrenia or a related psychotic disorder. In one embodiment the mental disorder is a treatment resistant schizophrenia.

In a further embodiment of the invention the treatment is targeted at a prodromal or residual phase of the schizophrenia or related disorder.

In accordance with an eight aspect of the present invention there is provided a method of treating a mental disorder, in which the subject is taking a typical or an atypical antipsychotic to treat symptoms of psychosis, further comprising administering cannabidiol (CBD) to said subject in an amount, and for the purpose of, treating anhedonia or asociality.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine or quetiapine.

Preferably the mental disorder is schizophrenia or a related psychotic disorder. More preferably the subject is deemed treatment resistant.

In a further embodiment of the invention the treatment is targeted at a prodromal or residual phase of the schizophrenia or related disorder.

Preferably the subject is a human.

In accordance with a ninth aspect of the present invention there is provided cannabidiol (CBD) as an adjunct medicament in the treatment of a mental disorder where psychotic symptoms are being treated with a typical or an atypical antipsychotic, characterised in that the CBD is for use in treating avolition/apathy.

Preferably the avolition/apathy is impersistence at work or school.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine.

Preferably the mental disorder is schizophrenia or a related psychotic disorder. In one embodiment the mental disorder is a treatment resistant schizophrenia.

In a further embodiment of the invention the treatment is targeted at a prodromal or residual phase of the schizophrenia or related disorder.

In accordance with a tenth aspect of the present invention there is provided a method of treating a mental disorder, in which the subject is taking a typical or an atypical antipsychotic to treat symptoms of psychosis, further comprising administering cannabidiol (CBD) to said subject in an amount, and for the purpose of, treating avolition/apathy.

Preferably the avolition/apathy is impersistence at work or school.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine.

Preferably the mental disorder is schizophrenia or a related psychotic disorder. More preferably the subject is deemed treatment resistant.

In a further embodiment of the invention the treatment is targeted at a prodromal or residual phase of the schizophrenia or related disorder.

Preferably the subject is a human.

In accordance with an eleventh aspect of the present invention there is provided cannabidiol (CBD) as an adjunct medicament in the treatment of a mental disorder where psychotic symptoms are being treated with a typical or an atypical antipsychotic, characterised in that the CBD is for use in treating disturbance of attention.

Preferably the typical or atypical antipsychotic is aripiprazole or a metabolite thereof.

Preferably the mental disorder is schizophrenia or a related psychotic disorder. In one embodiment the mental disorder is a treatment resistant schizophrenia.

In a further embodiment of the invention the treatment is targeted at a prodromal or residual phase of the schizophrenia or related disorder.

In accordance with a twelfth aspect of the present invention there is provided a method of treating a mental disorder, in which the subject is taking a typical or atypical antipsychotic to treat symptoms of psychosis, further comprising administering cannabidiol (CBD) to said subject in an amount, and for the purpose of, treating disturbance of attention.

Preferably the typical or atypical antipsychotic is aripiprazole or a metabolite thereof.

Preferably the mental disorder is schizophrenia or a related psychotic disorder. More preferably the subject is deemed treatment resistant.

In a further embodiment of the invention the treatment is targeted at a prodromal or residual phase of the schizophrenia or related disorder.

Preferably the subject is a human.

In accordance with a thirteenth aspect of the present invention there is provided cannabidiol (CBD) for use in the treatment of a mental disorder, characterised in that the CBD is for use in treating negative symptoms selected from the group consisting of: avolition or apathy; anhedonia/asociality; and/or disturbance of attention and wherein the CBD is administered as a monotherapy or as an adjunct therapy to a typical or an atypical antipsychotic.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine, quetiapine or aripiprazole or a metabolite thereof.

Preferably the mental disorder is schizophrenia or a related psychotic disorder. In one embodiment the mental disorder is a treatment resistant schizophrenia.

In a further embodiment of the invention the treatment is targeted at a prodromal, active or residual phase of the schizophrenia or related disorder.

In accordance with a fourteenth aspect of the present invention there is provided a method of treating a mental disorder in which the subject is suffering from negative symptoms selected from the group consisting of: avolition or apathy; anhedonia/asociality; and/or disturbance of attention, comprising administering to a subject in need thereof cannabidiol (CBD) as a monotherapy or as an adjunct therapy to an antipsychotic.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine, quetiapine or aripiprazole or a metabolite thereof.

Preferably the mental disorder is schizophrenia or a related psychotic disorder. More preferably the subject is deemed treatment resistant.

In a further embodiment of the invention the treatment is targeted at a prodromal, active or residual phase of the schizophrenia or related disorder.

Preferably the subject is a human.

In accordance with a fifteenth aspect of the present invention there is provided cannabidiol (CBD) as an adjunct medicament in the treatment of a mental disorder, wherein psychotic symptoms are being treated with a typical or an atypical antipsychotic, characterised in that the CBD is for use in treating cognitive symptoms.

Preferably the cognitive symptoms are one or more of: working memory; motor speed; and/or executive functions.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine, quetiapine or aripiprazole or a metabolite thereof.

Preferably the mental disorder is schizophrenia or a related psychotic disorder. In one embodiment the mental disorder is a treatment resistant schizophrenia.

In a further embodiment of the invention the treatment is targeted at a prodromal, active or residual phase of the schizophrenia or related disorder.

In accordance with a sixteenth aspect of the present invention there is provided a method of treating a mental disorder, in which the subject is taking a typical or an atypical antipsychotic to treat symptoms of psychosis, further comprising administering cannabidiol (CBD) to said subject in an amount, and for the purpose of, treating cognitive symptoms.

Preferably the cognitive symptoms are one or more of: working memory; motor speed; and/or executive functions.

Preferably the typical or atypical antipsychotic is selected from the group consisting of: aripiprazole, olanzapine, risperidone, amisulpride, quetiapine, clozapine, flupentixol, zuclopentixol, paliperidone, and zisprasidone. More preferably the typical or atypical antipsychotic is olanzapine, quetiapine or aripiprazole or a metabolite thereof.

Preferably the mental disorder is schizophrenia or a related psychotic disorder. More preferably the subject is deemed treatment resistant.

In a further embodiment of the invention the treatment is targeted at a prodromal, active or residual phase of the schizophrenia or related disorder.

Preferably the subject is a human.

In accordance with a seventeenth aspect of the present invention there is provided a composition for use in the treatment of mental disorders comprising, as active agents cannabidiol (CBD) in combination with one or more antipsychotics selected from the group consisting of: olanzapine and quetiapine, together with one or more excipients.

The therapeutic dose range of the antipsychotic medicament olanzapine is between 5 and 20 mg/day orally; the therapeutic dose range of quetiapine is between 50 and 800 mg/day orally; and the therapeutic dose range of aripiprazole is between 10 and 30 mg/day orally.

Given the fact than the antipsychotic medicaments have a propensity to cause side effects and due to the fact that the data presented herein suggests a combination of CBD and antipsychotic medicaments have a greater than additive effect a lower than standard therapeutic range of antipsychotic medicaments may be used in the combination.

The therapeutic dose range of CBD is between 25 and 5000 mg/day orally.

Preferably the CBD used is in the form of a highly purified extract of *cannabis* such that the CBD is present at greater than 98% of the total extract (w/w) and the other components of the extract are characterised. In particular the cannabinoid tetrahydrocannabinol (THC) has been substantially removed, to a level of not more than 0.15% (w/w) and the propyl analogue of CBD, cannabidivarin, (CBDV) is present in amounts of up to 1%. Alternatively, the CBD may be a synthetically produced CBD.

In use when the CBD is used concomitantly with one or more other antipsychotic drugs the CBD may be formulated for administration separately, sequentially or simultaneously with the one or more antipsychotic drugs or the combination may be provided in a single dosage form. Where the CBD is formulated for administration separately, sequentially or simultaneously it may be provided as a kit or together with instructions to administer the one or more components in the manner indicated. The CBD may also be used as the sole medication, i.e. as a monotherapy.

Preferably, the CBD combined with the antipsychotic medicament is formulated as a pharmaceutical composition further comprising one or more pharmaceutically acceptable carriers, excipients or diluents. The CBD and antipsychotic medicaments may be formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

Suitable dosage forms include, but are not limited to, solid dosage forms, for example tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Liquid dosage forms also include solutions or sprays for intranasal, buccal or sublingual administration. Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range of from 25 mg to 5000 mg per unit dose.

Metabolites of aripiprazole are included within the scope of the present invention. One such metabolite of aripiprazole is called dehydroaripiprazole. Preferred metabolites of aripiprazole included within the present invention are indicated by the following designations: OPC-14857, DM-1458, DM-1451, DM-1452, DM-1454 and DCPP.

Aripiprazole and aripiprazole metabolites to be used in the present invention may be any of from, for example, free bases, polymorphisms of every type of crystal, hydrate, salts (acid addition salts, etc.) and the like. Among of these forms, anhydrous aripiprazole crystals B is a preferred form. As to method for preparing the anhydrous aripiprazole crystals B, for example it is prepared by heating aripiprazole hydrate A, the details of which are shown in WO2004/060374.

Definitions

Definitions of some of the terms used to describe the invention are detailed below:

The cannabinoids described in the present application are listed below along with their standard abbreviations.

TABLE 1

Cannabinoids and their abbreviations

| CBD | Cannabidiol | |

TABLE 1-continued

Cannabinoids and their abbreviations

| CBDV | Cannabidivarin |
| THC | Tetrahydrocannabinol |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example it is known that heating the carboxylic acid form will cause most of the carboxylic acid form to decarboxylate into the neutral form.

"Treatment-resistant schizophrenia" (TRS) is defined as an inadequate response to at least two antipsychotic drugs at the maximally tolerated dose within the recommended therapeutic range, in trials lasting six weeks or more.

The therapeutic dose range of the antipsychotic medicament olanzapine is between 5 and 20 mg/day orally; the therapeutic dose range of quetiapine is between 50 and 800 mg/day orally; and therapeutic dose range of aripiprazole is between 10 and 30 mg/day orally The therapeutic dose range of CBD is between 25 mg/day and 5000 mg/day orally.

"PANNS" is defined as the Positive and Negative Syndrome Scale rating criteria.

"SANS" is defined as the Scale for the Assessment of Negative Symptoms.

"BACS" is defined as the Brief Assessment of Cognition in Schizophrenia.

"Responder status" is defined as the percentage of patients that demonstrated a greater than or equal to 20% increase in change from baseline.

"Augmenting" is defined as increasing the effectiveness of the antipsychotic medication by adding to its effect.

DETAILED DESCRIPTION

Preparation of Highly Purified CBD Extract

The following describes the production of the highly-purified (>98% w/w) cannabidiol extract which has a known and constant composition which was used for the clinical trials described in the Examples below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 98% CBD.

The *Cannabis sativa* L. plants are grown, harvested, and processed to produce a botanical extract (intermediate) and then purified by crystallization to yield the CBD (drug substance).

The plant starting material is referred to as Botanical Raw Material (BRM); the botanical extract is the intermediate; and the active pharmaceutical ingredient (API) is CBD, the drug substance.

Both the botanical starting material and the botanical extract are controlled by specifications. The drug substance specification is described in Table 2 below.

TABLE 2

CBD Specification

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| Other Cannabinoids: | HPLC-UV | |
| CBDA | | NMT 0.15% w/w |
| CBDV | | NMT 1.0% w/w |
| $\Delta^9$ THC | | NMT 0.15% w/w |
| CBD-C4 | | NMT 0.5% w/w |
| Residual Solvents: | GC | |
| Alkane | | NMT 0.5% w/w |
| Ethanol | | NMT 0.5% w/w |
| Residual Water | Karl Fischer | NMT 1.0% w/w |

NMT—Not more than

The purity of the CBD drug substance achieved is greater than 98%. The other cannabinoids which may occur in the extract are: CBDA, CBDV, CBD-C4 and THC.

Distinct chemotypes of *Cannabis sativa* L. plant have been produced to maximize the output of the specific chemical constituents, the cannabinoids. One type of plant produces predominantly CBD. Only the (−)-trans isomer occurs naturally. Furthermore during purification the stereochemistry of CBD is not affected.

Production of the Intermediate

An overview of the steps to produce a botanical extract, the intermediate, are as follows:
1. Growing
2. Decarboxylation
3. Extraction No. 1—using liquid $CO_2$
4. Extraction No. 2—'winterization' using ethanol
5. Filtration
6. Evaporation High CBD chemovars were grown, harvested and dried and stored in a dry room until required. The botanical raw material (BRM) was finely chopped using an Apex mill fitted with a 1 mm screen. The milled BRM was stored in a freezer for up to 3 months prior to extraction.

Decarboxylation of CBDA to CBD was carried out using a large Heraeus tray oven. The decarboxylation batch size in the Heraeus is approximately 15 Kg. Trays were placed in the oven and heated to 105° C.; the BRM took 96.25 minutes to reach 105° C. Held at 105° C. for 15 Minutes. Oven then set to 150° C.; the BRM took 75.7 minutes to reach 150° C.; BRM held at 150° C. for 130 Minutes. Total time in the oven was 380 Minutes, including 45 minutes cooling and 15 Minutes venting.

Extraction No 1 was performed using liquid $CO_2$ at 60 bar/10° C. to produce botanical drug substance (BDS).

The crude CBD BDS was winterised in Extraction No 2 under standard conditions (2 volumes of ethanol at minus 20° C. for around 50 hours). The precipitated waxes were removed by filtration and the solvent evaporated using the rotary evaporator (water bath up to 60° C.) to yield the BDS, which was then used for crystallisation to produce the test material.

Production of the Drug Substance

The manufacturing steps to produce the drug substance from the intermediate botanical extract are as follows:

Crystallization using C5-C12 straight chain or branched alkane

Filtration

Optional recrystallization from C5-C12 straight chain or branched alkane

Vacuum drying

Intermediate botanical extract (12 kg) produced using the methodology above was dispersed in C5-C12 straight chain or branched alkane (9000 ml, 0.75 vols) in a 30 litre stainless steel vessel.

The mixture was manually agitated to break up any lumps and the sealed container then placed in a freezer for approximately 48 hours.

The crystals were isolated by vacuum filtration, washed with aliquots of cold C5-C12 straight chain or branched alkane (total 12000 ml), and dried under a vacuum of <10 mb at a temperature of 60° C. until dry before submitting the drug substance for analysis.

The dried product was stored in a freezer at minus 20° C. in a pharmaceutical grade stainless steel container, with FDA food grade approved silicone seal and clamps.

Production of the Drug Product

The drug product is presented as an oral solution. The oral solution presentation contains 25 mg/ml or 100 mg/ml CBD, with the excipients sesame oil, ethanol, sucralose and flavouring. Two product strengths are available to allow dose titration across a wide dose range.

The 25 mg/ml solution is appropriate at lower doses and the 100 mg/ml solution at higher doses.

The drug product formulation is as described in Table 3 below:

TABLE 3

| Drug Product specification | | | |
|---|---|---|---|
| Component | Qualitative Composition | Function | Reference to Quality Standard |
| Cannabidiol (CBD) | 25 mg/ml or 100 mg/ml | Active | In-house |
| Anhydrous ethanol | 79.0 mg/ml | Excipient | Ph. Eur. |
| Sucralose | 0.5 mg/ml | Sweetener | In-house |
| Strawberry flavouring | 0.2 mg/ml | Flavouring | In-house |
| Sesame oil | q.s to 1.0 ml | Excipient | Ph. Eur. |

The drug substance, CBD is insoluble in water. Sesame oil was selected as an excipient to solubilize the drug substance.

A sweetener and fruit flavouring are required to improve palatability of the sesame oil solution.

Ethanol was required to solubilize the sweetener and the flavouring.

The composition can be substantially equivalent, by which is meant the functional ingredients can vary from the qualitative composition specified in Table 3 by an amount of up to 10%.

Example 1 below describes the use of a highly purified *cannabis* extract comprising cannabidiol (CBD) in a human clinical trial. Example 1 describes data produced in a double-blind, randomised, placebo-controlled, parallel group study of highly purified CBD as adjunctive therapy in first line treatment of schizophrenia or related psychotic disorder.

Example 1: Efficacy of Cannabidiol as Adjunctive Therapy in First Line Treatment of Schizophrenia or Related Psychotic Disorder Materials and Methods An eight-week, multi-centre, double-blind, randomised, placebo-controlled, parallel group study was conducted with the aim to determine the efficacy, safety and tolerability of highly purified CBD as adjunctive therapy in first line treatment of schizophrenia or related psychotic disorder.

This study evaluated the efficacy of highly purified CBD compared with placebo on the participant's PANSS Total score, 'P', 'N', 'G', SANS and BACS scores.

Changes from baseline in PANSS scores (Total, 'P', 'N' and 'G'), SANS and BACS were recorded at the start of the study (baseline) and at the end of treatment (after 6 weeks treatment with CBD or placebo).

For inclusion in the study participants were required to be male or female aged 18 to 65 years, diagnosed with schizophrenia or a related psychotic disorder (such as schizoaffective or schizophreniform disorder) as defined by the Diagnostic and Statistical Manual of Mental Disorders Version 4. Participants must have been treated for a minimum of four-weeks and be on a stable dose of their current antipsychotic medication. Participants must also have a PANSS total score in excess of 60 and previously failed to respond to one or more first line antipsychotic medicaments. A PANSS score in excess of 60 infers that the patient has symptoms related to schizophrenia or related disorders.

The participants were randomised to one of two treatment groups which each consisted of 39 participants. Treatment was administered as either 5 ml CBD (100 mg/ml) oral solution to be taken twice daily or 5 ml matched placebo oral solution to be taken twice daily.

Questionnaire Completion

Positive and Negative Syndrome Scale (PANSS)

The PANSS is a medical scale completed by a trained rater and is used for measuring symptom severity of participants with schizophrenia or related psychotic disorder. The name refers to the two types of symptoms in schizophrenia, as defined by the American Psychiatric Association: positive symptoms, which refer to an excess or distortion of normal functions (e.g. hallucinations and delusions), and negative symptoms, which represent a diminution or loss of normal functions.

It is a 30 item rating instrument that assesses the positive and negative symptoms of schizophrenia as well as symptoms of general psychopathology. A PANSS Total score is derived from the sum of the 30 items and the PANSS items are also grouped into three subscales: Positive ('P'), Negative ('N'), and General ('G'). Individual items are rated on a seven point scale, where 1=absent and 7=extreme. This scale was measured at each assessment visit (Visit 1-4).

The minimum score PANSS scoring system is 30 and patients with a score of higher than 60 are considered to still be suffering psychotic symptoms.

PANSS 'P' scale measures the severity of:
i) Delusions
ii) Conceptual disorganisation
iii) Hallucinations
iv) Hyperactivity
v) Grandiosity
vi) Suspiciousness/persecution
vii) Hostility PANSS 'N' scale measures the severity of:
i) Blunted affect
ii) Emotional withdrawal
iii) Poor rapport
iv) Passive/apathetic social withdrawal
v) Difficulty in abstract thinking
vi) Lack of spontaneity and flow of conversation
vii) Stereotyped thinking PANSS 'G' psychopathology scale measures the severity of:
i) Somatic concern
ii) Anxiety
iii) Guilt feelings
iv) Tension
v) Mannerisms and posturing
vi) Depression
vii) Motor retardation
viii) Uncooperativeness
ix) Unusual thought content
x) Disorientation
xi) Poor attention
xii) Lack of judgment and insight
xiii) Disturbance of volition
xiv) Poor impulse control
xv) Preoccupation
xvi) Active social avoidance Scale for the Assessment of Negative Symptoms (SANS)

SANS assesses five symptom complexes to obtain clinical ratings of negative symptoms in participants with schizophrenia or related psychotic disorder. They are: affective blunting; alogia (impoverished thinking); avolition/apathy; anhedonia/asociality; and disturbance of attention.

Assessments are conducted on a six-point scale (0=not at all to 5=severe). This scale was measured at each assessment visit (Visit 1-4)

Brief Assessment of Cognition in Schizophrenia (BACS)

The BACS is an instrument used to assess the aspects of cognition found to be most impaired and most strongly correlated with outcome in participants with schizophrenia or related psychotic disorder. The BACS yields a high completion rate in participants with schizophrenia or related psychotic disorder.

The BACS consists of six domains: verbal memory; working memory; motor speed; verbal fluency; attention and speed information processing and executive functions. A score is obtained for each domain and a composite summary score is also calculated as the average of the scores from the six domains. An increase in score is indicative of an improvement in cognition.

This instrument was assessed at each assessment visit (Visits 1-4).

Results

The change in baseline scores recorded for the participants taking CBD or placebo are summarised in Tables 4a and 4b below.

TABLE 4a

Change in baseline scores for CBD or placebo

| | CBD | Placebo | P-value (difference) |
|---|---|---|---|
| PANSS total score | −11.4 | −8.6 | P = 0.1332 (−2.8) |
| PANSS 'P' score | −3.1 | −1.8 | P = 0.0188 (−1.4) |
| PANSS 'N' score | −3.1 | −3.0 | P = 0.8841 (−0.1) |
| PANSS 'G' score | −5.3 | −4.0 | P = 0.1963 (−1.3) |
| SANS total score | −9.5 | −5.9 | P = 0.1168 (−3.5) |
| BACS composite score | 3.5 | 2.2 | P = 0.0677 (1.3) |
| BACS sub-domain 1 Verbal memory | 2.1 | 2.0 | P = 0.9933 (0.1) |
| BACS sub-domain 2 Working memory | 1.8 | 0.8 | P = 0.1414 (1.0) |
| BACS sub-domain 3 Motor speed | 6.2 | 2.0 | P = 0.0439 (4.2) |
| BACS sub-domain 4 Verbal fluency | 4.3 | 3.9 | P = 0.8059 (0.4) |
| BACS sub-domain 5 Attention and speed information processing | 4.4 | 3.5 | P = 0.5915 (0.9) |
| BACS sub-domain 6 Executive function | 2.0 | 0.6 | P = 0.0682 (1.4) |

Table 4a shows that when the data from the two groups, active and placebo, were compared using analysis of covariance a statistically significant P-value was found in the PANSS 'P' score for participants treated with CBD. This was very surprising given the patients were considered to be treatment resistant patients.

It was also observed that the BACS composite score approached statistical significance and for the sub-domain of motor speed a statistically significant P-value was recorded. Additionally, in the sub-domains of working memory and executive function a near statistically significant result was observed.

TABLE 4b

Responder status for change in baseline scores for CBD or placebo

|  | CBD (%) | Placebo (%) | P-value |
|---|---|---|---|
| PANSS total score | 28.6 | 13.6 | P = 0.0896 |
| PANSS 'P' score | 42.9 | 22.7 | P = 0.0679 |
| PANSS 'N' score | 26.2 | 25.0 | P = 0.7951 |
| PANSS 'G' score | 28.6 | 18.2 | P = 0.2598 |

Table 4b shows that at the end of the treatment period, 28.6% of patients taking CBD were deemed to be responders to the PANSS questionnaire as a whole.

Furthermore a 42.9% of participants demonstrated a response for the positive questions from the PANSS questionnaire.

Assessment of Concomitant Antipsychotic Medication

In order to assess the concomitant use of CBD with existing antipsychotic medication the data were analysed to determine the individual scores related to the different types of existing antipsychotic medication that the participant was taking during the study.

The participants in the study were all taking one of the following medicaments; aripiprazole, olanzapine, risperidone, amisulpride, quetiapine, clozapine, flupentixol, zuclopentixol, paliperidone, and zisprasidone. Data are presented for aripiprazole, olanzapine, risperidone, amisulpride, and quetiapine. The number of participants taking clozapine, flupentixol, zuclopentixol, paliperidone, and zisprasidone were too small for individual analysis and the data for these medicaments are therefore represented under the heading "other".

The following tables (Tables 5 to 7) detail these findings.

TABLE 5

Change in baseline scores for CBD or placebo on PANSS total

|  | CBD | Placebo | P-value (difference) |
|---|---|---|---|
| All patients | −11.4 | −8.6 | P = 0.1332 (−2.8) |
| Aripiprazole | −12.3 | −6.1 | P = 0.1220 (−6.2) |
| Olanzapine | −17.5 | −6.8 | P = 0.0067 (−10.7) |
| Risperidone | −7.8 | −9.6 | P = 0.6470 (1.8) |
| Amisulpride | −11.3 | −19.2 | P = 0.5543 (7.9) |
| Quetiapine | −7.5 | −12.5 | P = 0.6640 (5.1) |
| Other | −10.3 | 0.3 | P = 0.2746 (−10.6) |

These data demonstrate that the combination of CBD with olanzapine produced a statistically significant PANSS total in comparison to all the other antipsychotic medicaments that were used concomitantly during the study. This surprising result suggests that the combination of CBD plus olanzapine would be beneficial in the holistic treatment of schizophrenia or related psychotic disorders i.e. treating not only positive but also the negative and general symptoms of, for example, schizophrenia.

TABLE 6

Change in baseline scores for CBD or placebo on PANSS 'P' score

|  | CBD | Placebo | P-value (difference) |
|---|---|---|---|
| All patients | −3.1 | −1.8 | P = 0.0188 (−1.4) |
| Aripiprazole | −3.8 | −0.8 | P = 0.0345 (−3.1) |
| Olanzapine | −3.9 | −2.5 | P = 0.1434 (−1.5) |
| Risperidone | −2.6 | −1.8 | P = 0.4625 (−0.8) |
| Amisulpride | −4.0 | −3.5 | P = 0.8241 (−0.5) |
| Quetiapine | −1.7 | −2.3 | P = 0.7905 (0.6) |
| Other | −1.4 | −1.2 | P = 0.9550 (−0.2) |

As can be seen from Table 6 the combination of CBD and aripiprazole was statistically significant in comparison to the combination with other antipsychotic medicaments. This surprising result suggests that the combination of CBD with aripiprazole may be beneficial in the treatment or reduction in severity of the positive symptoms associated with schizophrenia or related psychotic disorder. Such symptoms include: Delusions; Conceptual disorganisation; Hallucinations; Hyperactivity; Grandiosity; Suspiciousness/persecution; and Hostility.

TABLE 7

Change in baseline scores for CBD or placebo on SANS score

|  | CBD | Placebo | P-value (difference) |
|---|---|---|---|
| All patients | −9.5 | −5.9 | P = 0.1168 (−3.5) |
| Aripiprazole | −4.7 | −3.3 | P = 0.7642 (−1.4) |
| Olanzapine | −20.5 | −6.3 | P = 0.0050 (−14.3) |
| Risperidone | −3.6 | −6.7 | P = 0.2955 (3.1) |
| Amisulpride | −2.4 | −19.1 | P = 0.0687 (16.6) |
| Quetiapine | −10.4 | −5.0 | P = 0.3150 (−5.4) |
| Other | −10.6 | −2.3 | P = 0.3359 (−8.3) |

Table 7 details the statistical significant result obtained from the combination of CBD with olanzapine on the reduction of severity of the SANS score. Such a combination could therefore be successful in the reduction of negative symptoms recorded by the SANS system which include: affective blunting; alogia (impoverished thinking); avolition/apathy; anhedonia/asociality; and disturbance of attention. This surprising finding has significant implications for treatment.

Assessment of Data Produced by SANS Sub-Scales

The five sub-scales within SANS were analysed further in order to assess whether the combination of CBD with antipsychotic medicaments could be of benefit to specific aspects of the negative symptoms.

Tables 8 and 9 detail the changes in baseline for sub-scale 4 (anhedonia/asociality) and sub-scale 5 (disturbance of attention).

TABLE 8

Change in baseline scores for CBD or placebo on SANS sub-scale 4

| | CBD | Placebo | P-value (difference) |
|---|---|---|---|
| All patients | −1.9 | −0.7 | P = 0.0605 (−1.2) |
| Aripiprazole | −0.2 | 0.3 | P = 0.7086 (−0.5) |
| Olanzapine | −4.9 | −1.1 | P = 0.0071 (−3.7) |
| Risperidone | −0.4 | −1.7 | P = 0.2800 (1.2) |
| Amisulpride | −0.1 | −1.4 | P = 0.4357 (1.4) |
| Quetiapine | −5.1 | −0.4 | P = 0.0017 (−4.8) |
| Other | −1.2 | −0.3 | P = 0.5465 (−0.8) |

Table 8 demonstrates that surprisingly the combination of CBD with olanzapine or CBD with quetiapine were able to produce statistically significant changes in baseline for the improvement of symptoms associated with SANS sub-scale 4. The concomitant use of CBD with either olanzapine or quetiapine might be beneficial in the treatment of specific negative symptoms in schizophrenia or associated disorders, namely anhedonia and asociality.

TABLE 9

Change in baseline scores for CBD or placebo on SANS sub-scale 5

| | CBD | Placebo | P-value (difference) |
|---|---|---|---|
| All patients | −1.6 | −0.9 | P = 0.0660 (−0.7) |
| Aripiprazole | −1.3 | −0.3 | P = 0.1133 (−1.0) |
| Olanzapine | −2.5 | −1.5 | P = 0.3556 (−1.0) |
| Risperidone | 0.1 | −0.6 | P = 0.3302 (0.7) |
| Amisulpride | −1.0 | −2.3 | P = 0.4023 (1.3) |
| Quetiapine | −1.8 | −0.8 | P = 0.2701 (−1.1) |
| Other | −2.5 | −1.0 | P = 0.4192 (−1.5) |

Table 9 demonstrates that the data collated for all participants produced a near statistical significant result. Thus the use of CBD may be of benefit in the treatment of specific negative symptoms in schizophrenia or associated disorders, namely disturbance of attention.

Assessment of Data Produced by SANS Specific Symptoms

In order to determine whether the use of CBD was of benefit to specific symptoms of the negative assessment scale further data analysis was conducted on specific questions contained within the SANS questionnaire.

Table 10 describes the data from SANS question 15, which falls under sub-scale 3 (avolition/apathy), Tables 11 to 15 describe the data from SANS questions 18 to 22 respectively, which fall under sub-scale 4 (anhedonia/asociality) and finally Tables 16 to 18 describe the data from SANS questions 23 to 25 which fall under sub-scale 5 (disturbance of attention).

Avolition/Apathy

TABLE 10

Change in baseline scores for CBD or placebo on SANS question 15: Impersistence at work or school

| | CBD | Placebo | P-value (difference) |
|---|---|---|---|
| All patients | −0.5 | −0.1 | P = 0.0187 (−0.4) |
| Aripiprazole | −0.3 | 0.2 | P = 0.1966 (−0.5) |
| Olanzapine | −1.2 | −0.3 | P = 0.0242 (−0.9) |
| Risperidone | −0.3 | −0.4 | P = 0.6285 (0.1) |
| Amisulpride | −0.5 | −0.5 | P = 0.8729 (0.0) |
| Quetiapine | −7.5 | −12.5 | P = 0.6640 (5.1) |
| Other | −10.3 | 0.3 | P = 0.2746 (−10.6) |

Table 10 details that all participants in the study who were taking CBD demonstrated a statistically significant change in baseline for an improvement of impersistence at work or school. In particular the combination of CBD with olanzapine was of statistical significance.

These data suggest treatment with CBD (with or without olanzapine) in patients who are suffering from schizophrenia or a related disorder may result in an improvement of the negative symptoms associated with impersistence at work or school. Again these results are surprising.

Anhedonia/Asociality

TABLE 11

Change in baseline scores for CBD or placebo on SANS question 18: Recreational interests and activity

| | CBD | Placebo | P-value (difference) |
|---|---|---|---|
| All patients | −0.6 | −0.3 | P = 0.1535 (−0.3) |
| Aripiprazole | −0.1 | 0.2 | P = 0.2979 (−0.3) |
| Olanzapine | −1.3 | −0.5 | P = 0.0689 (−0.8) |
| Risperidone | −0.3 | −0.6 | P = 0.4560 (−0.3) |
| Amisulpride | 0.0 | −1.0 | P = 0.3833 (1.0) |
| Quetiapine | −1.3 | 0.0 | P = 0.0233 (−1.3) |
| Other | −0.4 | −0.2 | P = 0.8182 (−0.1) |

Table 11 demonstrates that the combination of CBD with quetiapine produced a statistically significant change in baseline score for participants recreational interests and activity. There was also a nearly statistical significant result obtained from the combination of CBD with olanzapine.

These data suggest that surprisingly co-treatment of CBD with quetiapine or olanzapine may help reduce the negative symptoms associated with lack of interest in activities or hobbies and a patient's intractable inability to become involved in or enjoy activities.

TABLE 12

Change in baseline scores for CBD or placebo on
SANS question 19: Sexual interest and activity

|  | CBD | Placebo | P-value (difference) |
|---|---|---|---|
| All patients | −0.4 | 0.0 | P = 0.0364 (−0.4) |
| Aripiprazole | −0.1 | 0.2 | P = 0.4231 (−0.3) |
| Olanzapine | −1.0 | −0.1 | P = 0.0794 (−0.9) |
| Risperidone | 0.0 | −0.1 | P = 0.6889 (0.1) |
| Amisulpride | 0.0 | 0.8 | P = 0.1971 (−0.8) |
| Quetiapine | −1.5 | 0.0 | P = 0.0501 (−1.4) |
| Other | −0.3 | −0.3 | P = 0.9656 (0.0) |

Table 12 details that surprisingly all participants in the study who were taking CBD demonstrated a statistically significant change in baseline for an increase in sexual activity and interest. In particular the combination of CBD with quetiapine was of significance and the combination of CBD with olanzapine was also nearing statistical significance.

These data suggest treatment with CBD (with or without quetiapine or olanzapine) in patients who are suffering from schizophrenia or a related disorder may result in an improvement of the negative symptoms associated with lack of sexual interest and enjoyment.

TABLE 13

Change in baseline scores for CBD or placebo on SANS
question 20: Ability to feel closeness and intimacy

|  | CBD | Placebo | P-value (difference) |
|---|---|---|---|
| All patients | −0.3 | 0.0 | P = 0.0918 (−1.1) |
| Aripiprazole | 0.0 | 0.0 | P = 0.8965 (0.0) |
| Olanzapine | −1.0 | −0.1 | P = 0.0069 (−0.9) |
| Risperidone | 0.0 | 0.0 | P = 0.8648 (0.0) |
| Amisulpride | −0.1 | −0.2 | P = 0.8772 (0.1) |
| Quetiapine | −0.4 | −0.1 | P = 0.1330 (−0.4) |
| Other | −0.1 | 0.3 | P = 0.2601 (−0.4) |

Table 13 details that all participants in the study who were taking CBD demonstrated a near statistically significant change in baseline for an increase in their ability to feel intimacy and closeness. Surprisingly, the combination of CBD with olanzapine was of significance.

These data suggest treatment with CBD (with or without olanzapine) in patients who are suffering from schizophrenia or a related disorder may result in an improvement of the negative symptoms associated with lack of ability to form close and intimate relationships.

TABLE 14

Change in baseline scores for CBD or placebo on SANS
question 21: Relationships with friends and peers

|  | CBD | Placebo | P-value (difference) |
|---|---|---|---|
| All patients | −0.3 | −0.3 | P = 0.8984 (0.0) |
| Aripiprazole | −0.1 | 0.0 | P = 0.8346 (−0.1) |
| Olanzapine | −0.6 | −0.3 | P = 0.4829 (−0.2) |
| Risperidone | −0.1 | −0.6 | P = 0.0791 (0.5) |
| Amisulpride | −0.1 | −0.6 | P = 0.5671 (0.5) |
| Quetiapine | −0.7 | 0.0 | P = 0.0044 (−0.7) |
| Other | −0.2 | 0.0 | P = 0.6373 (−0.2) |

Table 14 details that participants in the study who were taking CBD in combination with quetiapine surprisingly demonstrated a statistically significant change in baseline for an increase in their relationships with friends and peers.

These data suggest treatment with CBD in combination with quetiapine in patients who are suffering from schizophrenia or a related disorder may result in an improvement of the negative symptoms associated with lack of ability to form relationships meaning that the untreated patient spends most or all of their time alone.

TABLE 15

Change in baseline scores for CBD or placebo on
SANS question 22: Global rating of anhedonia

|  | CBD | Placebo | P-value (difference) |
|---|---|---|---|
| All patients | −0.3 | −0.1 | P = 0.1787 (−0.2) |
| Aripiprazole | 0.0 | 0.0 | P = 0.9259 (0.0) |
| Olanzapine | −0.8 | −0.2 | P = 0.0475 (−0.6) |
| Risperidone | −0.2 | −0.2 | P = 0.9940 (0.0) |
| Amisulpride | −0.1 | −0.2 | P = 0.8772 (0.1) |
| Quetiapine | −1.3 | −0.2 | P = 0.1043 (−1.1) |
| Other | −0.2 | 0.0 | P = 0.6969 (−0.2) |

Table 15 details that participants in the study who were taking CBD in combination with olanzapine surprisingly demonstrated a statistically significant change in baseline for an increase in their global rating of anhedonia.

These data suggest treatment with CBD in combination with olanzapine in patients who are suffering from schizophrenia or a related disorder may result in an improvement of the negative symptoms associated with anhedonia.

Disturbance of Attention

TABLE 16

Change in baseline scores for CBD or placebo
on SANS question 23: Social inattentiveness

| | CBD | Placebo | P-value (difference) |
|---|---|---|---|
| All patients | −0.5 | −0.3 | P = 0.2445 (−0.2) |
| Aripiprazole | −0.4 | −0.2 | P = 0.3546 (−0.2) |
| Olanzapine | −0.9 | −0.7 | P = 0.6757 (−0.2) |
| Risperidone | 0.2 | 0.0 | P = 0.5207 (0.2) |
| Amisulpride | −0.1 | −0.6 | P = 0.4206 (0.5) |
| Quetiapine | −0.6 | −0.1 | P = 0.0862 (−0.5) |
| Other | −0.9 | −0.3 | P = 0.4246 (−0.5) |

Table 16 details that participants in the study who were taking CBD in combination with quetiapine demonstrated a statistically significant change in baseline for an improvement in their social inattentiveness.

These data suggest treatment with CBD in combination with quetiapine in patients who are suffering from schizophrenia or a related disorder may result in an improvement of the negative symptoms associated with social inattentiveness meaning that the untreated patient may seem to have poor concentration when playing games, reading or watching TV.

TABLE 17

Change in baseline scores for CBD or placebo on SANS question
24: Inattentiveness during mental status testing

| | CBD | Placebo | P-value (difference) |
|---|---|---|---|
| All patients | −0.6 | −0.3 | P = 0.0610 (−0.3) |
| Aripiprazole | −0.5 | −0.1 | P = 0.1740 (−0.4) |
| Olanzapine | −0.7 | −0.5 | P = 0.5922 (−0.2) |
| Risperidone | −0.1 | −0.4 | P = 0.4231 (0.3) |
| Amisulpride | −0.8 | −0.7 | P = 0.8060 (−0.2) |
| Quetiapine | −0.9 | −0.4 | P = 0.4421 (−0.6) |
| Other | −1.3 | 0.3 | P = 0.0654 (−1.6) |

Table 17 details that participants in the study who were taking CBD demonstrated a near statistically significant change in baseline for an improvement in their inattentiveness during mental status testing.

These data suggest treatment with CBD in patients who are suffering from schizophrenia or a related disorder may result in an improvement of the negative symptoms associated with inattentiveness during mental status testing meaning that the untreated patient may perform poorly on simple tests of intellectual functioning in spite of adequate education and intellectual ability.

TABLE 18

Change in baseline scores for CBD or placebo on
SANS question 25: Global rating of attention

| | CBD | Placebo | P-value (difference) |
|---|---|---|---|
| All patients | −0.5 | −0.2 | P = 0.0773 (−0.2) |
| Aripiprazole | −0.4 | 0.0 | P = 0.0412 (−0.4) |
| Olanzapine | −0.9 | −0.3 | P = 0.1064 (−0.6) |
| Risperidone | 0.0 | −0.2 | P = 0.3389 (0.2) |
| Amisulpride | 0.0 | −1.0 | P = 0.0756 (1.0) |
| Quetiapine | −0.5 | −0.1 | P = 0.2697 (−0.4) |
| Other | −0.3 | −1.1 | P = 0.1763 (0.8) |

Table 18 details that all participants in the study who were taking CBD demonstrated a near statistically significant change in baseline for an increase in global rating of attention. Surprisingly, the combination of CBD with aripiprazole produced a change in baseline that was of statistical significance.

These data suggest treatment with CBD (with or without aripiprazole) in patients who are suffering from schizophrenia or a related disorder may result in an improvement of the negative symptoms associated with lack of attentiveness.

CONCLUSIONS

These data indicate that CBD alone or in combination with certain antipsychotic medications was able to significantly reduce many of the symptoms in a high proportion of patients that do not respond well to existing antipsychotic treatments.

It was surprising that in this group of patients who had a PANSS score in excess of 60 or had previously failed a first line antipsychotic, showed statistically significant responses in a number of areas.

In particular it was noted that CBD in combination with particular antipsychotics, namely olanzapine, quetiapine or aripiprazole produced statistically significant and unexpected effects in a range of symptoms in patients with schizophrenia or related disorder.

This was particularly surprising as the combination of CBD with other antipsychotics such as risperidone or amisulpride did not produce any results of significance, indeed on some of the parameters measured such combinations were of detriment.

It was also surprising to note that CBD was able to treat the negative symptoms associated with schizophrenia as these symptoms are very difficult to treat; indeed there are no existing medications available to treat such symptoms in schizophrenia or related disorders.

It is also envisaged that subsets of patients with schizophrenia, including those at a prodromal phase and the paediatric population may also benefit from treatment with CBD alone or in combination with certain antipsychotic medicaments.

REFERENCES

Addington J, Cadenhead K S, Cannon T D, Cornblatt B, McGlashan T H, Perkins D O et al. North American prodrome longitudinal study: a collaborative multisite approach to prodromal schizophrenia research. Schizophr Bull 2007; 33 (3): 665-72

Castle E; Wessely S, Der G, Murray R M. The incidence of operationally defined schizophrenia in Camberwell 1965-84. Br J Psychiatry 1991; 159: 790-4.

Cohen A S, Docherty N M. Affective reactivity of speech and emotional experience in patients with schizophrenia. Schizophr Res 2004; 69 (1): 7-14.

De Marchi N, De Petrocellis L, Orlando P, Daniele F, Fezza F, Di Marzo V. Endocannabinoid signalling in the blood of patients with schizophrenia. Lipids Health Dis 2003; 2: 5 FDA (2006)

Deiana S. Medical use of *cannabis*. Cannabidiol: A new light for schizophrenia? Drug testing and analysis 5(1) (2013) 46-51.

Foussias and Remington, Negative symptoms in schizophrenia: avolition and Occam's razor. Schizophr. Bull 2010 March: 36(2):359-69

Freeman D, Garety P A, Kuipers E, Fowler D, Bebbington P E, Dunn G. Acting on persecutory delusions: the importance of safety seeking. Behav Res Ther 2007; 45 (1): 89-99

Goldner E M, Hsu L, Waraich P, Somers J M. Prevalence and incidence studies of schizophrenic disorders: a systematic review of the literature. Can J Psychiatry 2002; 47 (9): 833-43.

Gomes F V., Llorente R., Del Bel E A., Decreased glial reactivity could be involved in the anti-psychotic-like effect of cannabidiol. Schizophrenia research. 164 (1-3) (2015) 155-163.

Gururajan A., Taylor, D A., Malone D T. Cannabidiol and clozapine reverse MK-801-induced deficits in social interaction and hyperactivity in Sprague-Dawley rats. Journal of Psychopharmacology 26(10) (2012). 1317-1332.

Iseger et al. A systematic review of the antipsychotic properties of cannabidiol in humans. Schizophrenia Research Laughren T. and Levin R., Food and Drug Administration Perspective on Negative Symptoms in Schizophrenia as a target for a Drug Treatment Claim. Schizophrenia Bulletin. 2006 April; 32(2): 220-222

Lindstrom L H. The effect of long-term treatment with clozapine in schizophrenia: A retrospective study in 96 patients treated with clozapine for up to 13 years. Acta Psychiatr Scand 1988; 77: 524-29

Miyamoto S, Duncan G E, Marx C E, Lieberman J A. Treatments for schizophrenia: a critical review of pharmacology and mechanisms of action of antipsychotic drugs. Mol Psychiatry 2005; 10: 79-104.

Robson P J, Guy G W, Di Marzo V. Cannabinoids and Schizophrenia: Therapeutic Prospects. Curr Pharm Des. 2014

Sergi Mark J., Rassovsky Yuri, Widmark Clifford, Reist Christopher, Erhart Stephen, Braff David L., Marder Stephen R., Green Michael F. Social cognition in schizophrenia: Relationships with neurocognition and negative symptoms. Schizophrenia Research 90 (2007) 316-324

Sims A. Symptoms in the Mind: An Introduction to Descriptive Psychopathology (3rd edition). Edinburgh 2002; Elsevier Science Ltd.

Taylor D. Cannabidiol reverses MK-801 induced social withdrawal in rats. Acta Pharmacologica Sinica 27(1) (2006). 78.

Zuardi A W., Crippa J A S., Dursun S M., Morais S L., Vilela J A A., Sanches R F., Hallak J E C. Cannabidiol was ineffective for manic episode of bipolar affective disorder. Journal of Psyhcopharmacology 24 (2) (2010) 135-137.

The invention claimed is:

1. A method of treating treatment resistant schizophrenia in a subject by augmenting the effect of a typical or an atypical antipsychotic, the method comprising administering to the subject cannabidiol (CBD) in combination with a typical or an atypical antipsychotic, wherein the amount of CBD administered augments the effect of the typical or atypical antipsychotic.

2. The method of claim 1, wherein the typical or atypical antipsychotic is selected from the group consisting of: aripiprazole, olanzapine, risperidone, amisulpride, quetiapine, clozapine, flupentixol, zuclopentixol, paliperidone, and zisprasidone.

3. The method of claim 2, wherein the typical or atypical antipsychotic is aripiprazole thereof.

4. The method of claim 1, wherein the treatment is targeted at an active phase of the schizophrenia.

5. A method of treating treatment resistant schizophrenia in a subject, the method comprising, administering to the subject, cannabidiol (CBD) in combination with one or more antipsychotics selected from the group consisting of: olanzapine and quetiapine, wherein the amount of CBD augments the effect of the one or more antipsychotics.

6. The method of claim 2, wherein the treatment is targeted at an active phase of the schizophrenia.

7. The method of claim 3, wherein the treatment is targeted at an active phase of the schizophrenia.

* * * * *